United States Patent [19]

Brannon

[11] 3,972,774

[45] Aug. 3, 1976

[54] ENZYMATIC DE-ESTERIFICATION OF CEPHALOSPORIN PARA-NITROBENZYL ESTERS

[75] Inventor: Donald Ray Brannon, Pittsboro, Ind.

[73] Assignee: Eli Lilly and Company, Indianapolis, Ind.

[22] Filed: July 28, 1975

[21] Appl. No.: 599,510

[52] U.S. Cl. .................................... 195/29; 195/30
[51] Int. Cl.² ........................................... C12C 9/04
[58] Field of Search ................. 195/30, 36 P, 80 R, 195/36 R, 96, 28 R, 29, 36 C

[56] References Cited

UNITED STATES PATENTS 3,749,641   7/1973   Takahashi et al. ............ 195/36 P X

*Primary Examiner*—A. Louis Monacell
*Assistant Examiner*—R. B. Penland
*Attorney, Agent, or Firm*—William C. Martens, Jr.; Everet F. Smith

[57] ABSTRACT

Cephalosporin p-nitrobenzyl esters are de-esterified via an esterase enzyme derived from the genus Bacillus.

23 Claims, No Drawings

ENZYMATIC DE-ESTERIFICATION OF CEPHALOSPORIN PARA-NITROBENZYL ESTERS

BACKGROUND OF THE INVENTION

In the course of the chemical modification of certain cephalosporin antibiotics it is often convenient to protect the reactive cephalosporin $C_4$ carboxylic acid function as a p-nitrobenzyl ester. The ester protecting group renders the carboxylic acid function inert to the various chemical operations performed on other parts of the cephalosporin molecule. Once the chemical operations have been accomplished, the p-nitrobenzyl group can be removed to provide the modified antibiotically active cephalosporin carboxylic acid.

Various chemical methods of removing ("deblocking") the p-nitrobenzyl group have been described in the cephalosporin literature. Such treatment involves a rigorous acid hydrolysis or, in some instances, hydrogenolysis. The unsubstituted benzyl group itself is cleaved by base and also by strongly acidic reagents, although the extent of hydrolysis with acids is variable and is dependent upon the concentration of acid and upon other conditions such as temperature and time. The effect of the electron attracting p-nitro substituent on the benzyl group is to stabilize the resulting p-nitrobenzyl ester towards acids. Thus p-nitrobenzyl esters display increased resistance to acid hydrolysis, hence more rigorous hydrolysis conditions are required. The particular attraction of this class of ester protecting groups for cephalosporin chemists lies undoubtedly in their ready removal by hydrogenolysis. For a resume of the methods of removal of benzyl ester protecting groups see J. F. W. McOmie, *Protective Groups in Organic Chemistry*, Plenum Press, London and New York, 1973, Chapter 5. The use of acid deblocking methods with certain cephalosporin p-nitrobenzyl esters, because of the rigorous acidic conditions, often produces polymeric impurities which make separation and purification of the final product difficult.

The p-nitrobenzyl cephalosporin esters (PNB esters) which are required as starting materials in the process of this invention can be prepared by the ring expansion of the corresponding penicillin sulfoxide PNB esters. The starting materials can be described, conveniently, by the structural formula

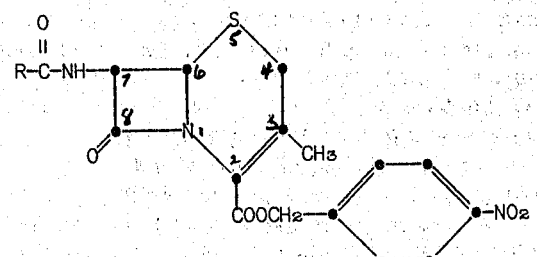

wherein R is the residue of the acyl group, for example, one derived from the penicillin sulfoxide PNB ester used. These starting materials can be prepared by the thermal rearrangement of the corresponding penicillin sulfoxide PNB esters as described in U.S. Pat. Nos. 3,275,626, 3,632,850 and 3,781,283. Numerous penicillins derived by fermentation methods known in the prior art (U.S. Pat. Nos. 2,379,295 and 2,479,297; 2,562,407 to 2,562,411; and 2,623,876) can be converted to PNB esters sulfoxides and rearranged to 7-acylamidocephem PNB esters. Alternatively the PNB ester starting materials can be prepared by esterifying the corresponding cephem-4-carboxylic acid intermediate with p-nitrobenzyl bromide in the presence of base and recovering the cephem-4-carboxylate PNB ester as described throughout the cephalosporin art.

Two highly useful cephalosporin intermediates are the p-nitrobenzyl esters of 7-(D-α-aminophenylacetamido)-3-methyl-3-cephem-4-carboxylic acid and 7-amino-3-methyl-3-cephem-4-carboxylic acid (7-ADCA). The former is significant because, upon cleavage of the p-nitrobenzyl group, the well recognized antibiotic, cephalexin, results; therefore, the p-nitrobenzyl ester finds great use as an intermediate to the preparation of cephalexin. The latter, the p-nitrobenzyl ester of 7-ADCA, is a useful intermediate in the preparation of active cephalosporin antibiotics. All the cephalosporin acid products derived by the process of this invention are known antibiotic substances described in the cephalosporin art.

Heretofore enzymatic methods for the removal of the p-nitrobenzyl ester protecting group from cephalosporin compounds have not been described. It is an object of this invention to provide an alternative process for the removal of the p-nitrobenzyl group from cephalosporin esters and particularly those which may be sensitive to chemical deblocking, particularly by acids.

SUMMARY OF THE INVENTION

This invention contemplates an enzymatic cleavage process for the removal of the p-nitrobenzyl group from a cephalosporin ester of the formula

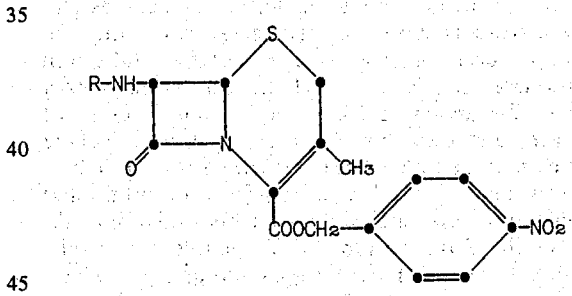

to provide a cephalosporin acid of the formula

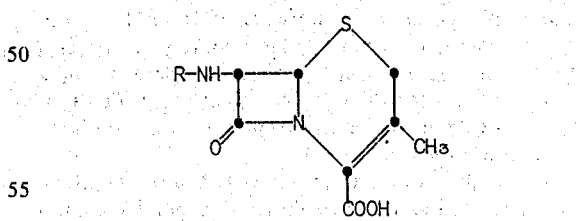

wherein R is hydrogen, 1,4-cyclohexadienylacetyl, mandeloyl, 4-aminophenylacetyl, 4-chlorophenylacetyl, 4-hydroxyphenylacetyl, phenylacetyl, 4-aminophenoxyacetyl, 4-chlorophenoxyacetyl, 4-hydroxyphenoxyacetyl, phenoxyacetyl, 4-aminophenylglycyl, 4-chlorophenylglycyl, 4-hydroxyphenylglycyl, phenylglycyl, 1-tetrazoleacetyl, 2-thiopheneacetyl, 3-thiopheneacetyl, or the hydrobromide, hydrochloride, nitrate, sulfate or tosylate salt thereof when R is hydrogen, phenylglycyl, 4-aminophenylglycyl, 4-chlorophenylglycyl or 4-hydroxyphenylglycyl; which comprises reacting said ester in an aqueous medium at 25° to 40°C. with an esterase enzyme produced by a microorganism of the genus Bacillus selected from the group consisting of *Bacillus cereus, Bacillus circulons, Bacillus licheniformis* and *Bacillus subtilis*, and recovering said cephalosporin acid.

DETAILED DESCRIPTION AND PREFERRED EMBODIMENTS

The enzymatic cleavage of this invention can be carried out by culturing a microorganism belonging to the genus Bacillus in the presence of the p-nitrobenzyl ester of a cephalosporin compound. Preferably, the microorganism is cultured to obtain a suitable cell population, the cells then are harvested, and the cleavage is carried out in a synthetic medium as described hereinafter. It is also possible to prepare from the appropriate genus Bacillus the esterase itself and this esterase can be employed directly in effecting cleavage of the p-nitrobenzyl group from the respective esters of cephalexin or 7-ADCA.

In any event, a seed culture of a microorganism of the genus Bacillus, which may be either a lyophilized culture or an agar culture is used to inoculate a small amount of a highly nutritious vegetative medium. The inoculated vegetative medium is then incubated until exponential growth of the bacterial population is achieved. The vegetative culture is then used as the inoculum for the larger scale fermentation.

The microorganism is cultured in an aqueous, nutrient culture medium containing assimilable sources of carbon, nitrogen, and inorganic salts. The fermentation is carried out under aerobic conditions. Sources of carbon can include, for example, sugars, such as glucose, sucrose, fructose, and maltose; however, the economical sources of sugar, such as molasses and starch hydrolysates can be used in large scale fermentation media. The amino acids provide suitable sources of nitrogen, and economic sources of nitrogen include beef extract, peptone, yeast extract, corn steep liquor, fish solubles, fish meal, casein hydrolysate broth, and the like. Inorganic salts which are employed as ingredients in the fermentation media include those salts which will supply the cations of sodium, potassium, calcium, ammonium, and the anions such as chloride, sulfate, phosphate and the like.

A preferred culture medium of this invention which can be employed as a vegetative medium and/or as a production medium contains approximately 1 percent peptone, one percent yeast extract, 0.5 percent beef extract, 0.45 percent L-glutamic acid, 0.25 Percent sodium chloride and 0.2 percent monopotassium phosphate in deionized water.

An agar culture or a lyophilized pellet of the Bacillus organism is used as the inoculum for a small volume, for example, from about 25 ml. to about 200 ml., of the vegetative medium. The medium is sterilized before use, and the pH is adjusted to a pH of about 7.0 to about 7.5 by addition, for example, of dilute sodium hydroxide. The inoculated culture then is incubated for about 16 to 60 hours at a temperature of about 25°C. to 40°C. During incubation, the fermentation flask is agitated, for example, by means of a rotary shaker. After the vegetative culture has grown into a mature population of cells, it then is used as the inoculum for the large scale fermentation medium. The fermentation medium can have the same composition as the vegetative culture medium, or its ingredients may include more economical nitrogen and carbon sources. The inoculated large scale fermentation medium then can be incubated at a temperature of about 25°C. to 40°C. for about 16 to 30 hours. During the period of fermentation, the fermentor is continually stirred and aerated.

Following the fermentation, the resulting bacterial cells are collected in a centrifuge. The harvested, wet cells are washed by gently stirring the cells in suspension in a phosphate buffer of pH 6 at a concentration of about 0.003 to 0.05 molar phosphate, for example. After washing, the cells are again collected by centrifugation, and the packed cells either are used directly for the enzymatic cleavage reaction or they are frozen for further use.

A lyophile pellet of each of the bacterial cultures listed in Table I was added to a 250 ml. Erlenmeyer flask containing 50 ml. of a 3 percent sterile Trypticase Soy Broth (Difco) medium. The cultures were incubated for about 24 to 48 hr. at 37°C. on a rotary shaker revolving at 250 rpm (2 inch diameter of arc). Five milliters of each culture was transferred to 20 ml. vials. To one set of vials was added an aqueous suspension of 5 mg. of cephalexin tosylate PNB ester. To the other set of vials was added an aqueous suspension of 5 mg. of 7-ADCA tosylate PNB ester. The vials were shaken for 24 hr. at 30°C. on a rotary shaker revolving at 250 rpm. The formation of antibiotic product in the two sets of vials was determined by an agar plate microbiological assay of the culture broths.

To measure the formation of cephalexin obtained from cephalexin tosylate PNB ester identical paper discs saturated with the culture broths were placed on two nutrient agar culture plates seeded with *Sarcina lutea*. One nutrient agar plate contained only the assay organism. The second seeded agar plate contained a crude preparation of cephalosporinase (cephase) in addition to the assay organism. Cephalosporinase is an enzyme which is capable of inactivating cephalosporin antibiotics by opening the $\beta$-lactam ring. The paper disc on the first seeded agar assay plate produced a zone of inhibition whereas no inhibition of *Sarcina lutea* was produced on the second seeded agar plate because of the destruction of cephalexin by cephase. This was also evidence that the inhibition was due specifically to a cephalosporin antibiotic because non $\beta$-lactam antibiotics are not significantly affected by cephase. The amount of cephalexin produced was determined by measuring the zone of growth inhibition obtained with the first assay plate. The quantity of cephalexin produced was then calculated by reference to a dose response plot for pure cephalexin.

The amount of 7-ADCA produced from 7-ADCA tosylate PNB ester was determined by the procedure described above except that the paper discs were subjected to phenoxyacetyl chloride vapors prior to plating them on assay plates seeded with *Bacillus subtilis*. The phenoxyacetyl chloride converted the 7-ADCA present on the discs to deacetoxycephalosporin V which was then assayed for antibiotic activity.

The identity of the antibiotics produced was confirmed by paper bioautographic comparison of each culture broth reaction sample with cephalexin or deacetoxycephalosporin V as a reference standard. The paper chromatography solvent system used for comparison with cephalexin was n-butanol:acetic acid:water (3:1:1). The solvent system used for comparison with deacetoxycephalosporin V was methyl ethyl ketone:water (92:8). Bioautographs of the paper chromatograms were obtained with the respective sensitive assay organism described above.

The Bacillus organisms which can be employed to produce esterases useful in the process of this invention are listed in Table I. Table I also summarizes the results obtained when p-nitrobenzyl 7-(D-α-aminophenylacetamido)-3-methyl-3-cephem-4-carboxylate and p-nitrobenzyl 7-amino-3-methyl-3-cephem-4-carboxylate are de-esterified by incubation with a mature culture of the respective organisms *Bacillus cereus*, *Bacillus circulons*, *Bacillus licheniformis* or *Bacillus subtilis*.

TABLE I

FORMATION OF CEPHALEXIN AND
7-ADCA BY BACTERIAL CULTURES

| Culture | Source | Product Formed, mcg./ml. | |
|---|---|---|---|
| | | Cephalexin[a] | 7-ADCA[b] |
| Bacillus subtilis | NRRL B558 | 40 | 49 |
| Bacillus circulons | ATCC 966 | 36.0 | 53 |
| Bacillus cereus | NRRL B569 | 29.0 | 39 |
| Bacillus licheniformis | ATCC 7072 | 2.5 | 140 |
| Bacillus cereus | ATCC 9634 | 15.6 | 19.5 |
| Bacillus cereus | NRRL B569 | 36 | 16 |
| Bacillus subtilis | NRRL B1471 | 31.2 | 94 |
| Bacillus subtilis | NRRL B8097 | 92 | 200 |
| Bacillus subtilis | ATCC 6633 | 250 | 170 |

[a]Determined by microbiological assay employing an agar plate seeded with *Sarcina lutea*.
[b]Determined by acylation of product 7-ADCA with phenoxyacetyl chloride and assay of the resulting deacetoxycephalosporin V with *Bacillus subtilis*.

The preferred organisms are the *Bacillus subtilis* cultures ATCC 6633, NRRL B1471, NRRL B8079 and NRRL B558. Especially preferred is *Bacillus subtilis* culture NRRL B8079. A culture of this new strain has been deposited, without restriction as to availability, with the permanent culture collection of the Northern Regional Research Laboratory, United States Department of Agriculture, 1815 North University Street, Peoria, Illinois 61604, where it was assigned the accession number NRRL B8079. *Bacillus subtilis* cultures NRRL B558 and NRRL B1471 are available from the same source. *Bacillus subtilis* culture accession number ATCC 6638 is available without restriction from the American Type Culture Collection, Rockville Maryland. The taxonomy of culture NRRL B8079 is given hereinbelow.

Microscopic Morphology of *B. subtilis* NRRL B8079

This bacterium is classified as a variety of *Bacillus subtilis*. It is a motile, spore-bearing rod which forms in chains of from 2 to 15 cells. Sporulation occurs readily on nutrient agar but is inhibited on agar supplemented with 1% dextrose. Motility is best observed in young cultures with single cells; however, motile pairs and triplets may occur. Sporulation occurs either terminally or centrally as endospores. The spores are generally elliptical but are frequently spherical.

These rod-shaped bacteria have slightly rounded ends and range from 1.83 $\mu$ to 3.28 $\mu$ long, averaging 2.53 $\mu$ × 1.0 $\mu$. Spherical spores are from 1.53 $\mu$ to 1.96 $\mu$ in diameter and average 1.68 $\mu$. Elliptical spores range from 1.48 $\mu$ to 1.61 $\mu$ long and from 1.02 $\mu$ to 1.08 $\mu$ wide, averaging 1.07 $\mu$ × 1.5 $\mu$. Sporangia are occasionally swollen to form spindles or wedge shapes. Free spores are rarely cylindrical with rounded ends.

*Bacillus subtilis* is described in *Bergey's Manual of Determinative Bacteriology*, 8th ed, R. E. Buchanan and N. E. Gibbons, Co-Ed., The Williams and Wilkins Co., Baltimore, Md., 1974. Culture NRRL B8079 differs from the description of *Bacillus subtilis* which is found in Bergey's Manual as follows: *B. subtilis* is generally not considered to produce a swollen sporangium; however, they are noted to have been observed. Bergey stresses the utilization of mannitol, arabinose, and xylose with the formation of acid without evolution of gas in an ammonium salts medium for *B. subtilis*. This factor occurs weakly in NRRL B8079. Sucrose is not utilized in the ammonium salts medium by B8079. This is not in agreement with Bergey's description of *B. subtilis*; however, sucrose in a peptone medium is utilized. According to Bergey anaerobic growth for *B. subtilis* is rare, possible microaerophilic, but NRRL B8079 is strictly aerobic. There is a greater tendency to form some gram negative cells in NRRL B8079 than might be indicated for *B. subtilis* by Bergey.

The nearest other possible specie is *B. brevis* which does not form chains, is less than 0.9 $\mu$ wide, is at least facultatively anaerobic, does not evolve acetylmethylcarbinol, does not hydrolyze starch, does not tolerate 10% NaCl, and does not utilize arabinose or xylose. These are eight major points which differ from NNRL B8079.

Cultural Characteristics of *B. subtilis* NRRL B8079

The optimum temperature of incubation is from 40°–45°C. Growth occurs weakly at 26°C. and moderately at 55°c., with no growth at 60°C.

On nutrient agar plates the culture may be a rapid spreader. Colonies are irregular, flat, smooth, glistening to dull, colorless, and mucoid to butyrous. They vary from translucent to opaque. Margins may show several concentric rings and the outer border is erose. Microscopically the colony is slightly granular. Occasionally small colonies are encountered on slants. Nutrient broth produces a white pellicle which might be slightly wrinkled or smooth with a thin white ring. The broth is only slightly turbid in 48 hours, with scant sedimentation. Nutrient agar slants are smooth to slightly wrinkled and a yellowish white. Addition of 1% dextrose may increase the growth with a tendency to heavier wrinkling and prevents rapid sporulation. On nutrient agar sporulation is heavy in 16 to 18 hours.

Carbohydrates are utilized without gas production in both a medium with ammonium salts or protein as a source of nitrogen. In beef extract-peptone broth glucose, fructose, glactose, and mannose acidic, and arabinose, xylose, and salicin are weakly acid. Lactose becomes alkaline. Growth with no observable pH change occurs in rhamnose, sucrose, starch, mannitol and dulcitol. With ammonium salts, no acid occurs in galactose and mannitol becomes weakly acid.

Glucose-ammonium salts support aerobic growth, but no growth is seen in a nitrogen/carbon dioxide atmosphere or when layered with sterile mineral oil. No growth is seen in agar stabs of nutrient, citrate, or Kligler's agars.

Catalase is produced. Gelatin is liquified slowly. Nitrates are reduced to nitrites. Citrates are utilized without gas production. No hydrogen sulfide is evolved on Kligler's iron agar. Litmus milk is peptonized with some curd formation and becomes alkaline. Acetylmethylcarbinol is produced. No indole is produced from tryptone or casein. Casein and starch are hydrolyzed. Growth occurs in 10% NaCl-nutrient broth. Growth on tyrosine agar is restricted producing no spores.

Alternatively the process of this invention can be carried out by isolating the enzyme produced by the appropriate Bacillus organisms. The cells of the mature culture are collected and sonicated to rupture the vegetative cells. The sonicated cells are collected by centrifugation and suspended in phosphate buffer. The cell suspension is dialyzed against phosphate buffer and the resulting dialyzate is lyophilized to give the crude esterase preparation. Then, following the process of this invention, the appropriate cephalosporin PNB ester and esterase enzyme preparation are incubated at preferably 30°C. for about 18 hours in pohsphate buffer, pH 6.8. After completion of the de-esterification procedure, the pH of the mixture is adjusted to 2.5 with 0.1N hydrochloric acid and the mixture is chromatographed with XAD-4 resin. The de-esterified cephalosporin product is adsorbed on the column. The column is washed with water and the product is then eluted with methanol. Concentration of the methanol eluate provides the desired de-esterified cephalosporin acid.

It should be noted that the process of this invention does not cleave the 7-ayclamido moiety of the cephalosporin compounds employed. Thus, there is virtually no limitation imposed on the process of this invention by the nature of the 7-acyl substituent. However, the esterase enzyme may cause the cleavage of other ester protecting groups which are an integral part of the 7-acyl moiety. For example, the PNB ester of 7-(0-formylmandeloyl)-3-methyl-4-cephemcarboxylic acid can be enzymatically de-esterified to provide 7-mandeloyl-3-methyl-4-cephem carboxylic acid, a known antibiotic.

The required cephalosporin PNB esters need only be partially soluble in the aqueous reaction medium. However, the use of ester salts which increase water solubility is advantageous. As the cephalosporin compound is de-esterified, the cephalosporin carboxylic acid product goes into solution. The de-esterification proceeds until the the less soluble PNB ester is consumed. However, if the de-esterification is incomplete, the unreacted ester and the de-esterified product are easily separated by methods such as filtration, extraction or chromatography. The antibiotically active de-esterified cephalosporin acid is recovered by methods known to the art.

Illustrative of the cephalosporin esters which can be employed in the process of this invention are the following:

p-Nitrobenzyl 7-amino-3-methyl-3-cephem-4-carboxylate hydrochloride.
p-Nitrobenzyl 7-amino-3-methyl-3-cephem-4-carboxylate tosylate
p-Nitrobenzyl 7-(1,4-cyclohexadienylacetamido)-3-methyl-3-cephem-4-carboxylate
p-Nitrobenzyl 7-mandelamido-3-methyl-3-cephem-4-carboxylate
p-Nitrobenzyl 7-[(4-aminophenyl) acetamido]-3-methyl-3-cephem-4-carboxylate
p-Nitrobenzyl 7-[(4-chlorophenyl) acetamido]-3-methyl-3-cephem-4-carboxylate
p-Nitrobenzyl 7-[(4-hydroxyphenyl) acetamido]-3-methyl-3-cephem-4-carboxylate
p-Nitrobenzyl 7-(phenylacetamido)-3-methyl-3-cephem-4-carboxylate
p-Nitrobenzyl 7-[(4-aminophenoxy)acetamido]-3-methyl-3-cephem-4-carboxylate
p-Nitrobenzyl 7-[(4-chlorophenoxy)acetamido]-3-methyl-3-cephem-4-carboxylate
p-Nitrobenzyl 7-[(4-hydroxyphenoxy)acetamido]-3-methyl-3-cephem-4-carboxylate
p-Nitrobenzyl 7-(phenoxyacetamido)-3-methyl-3-cephem-4-carboxylate
p-Nitrobenzyl 7-[$\alpha$-amino(4-chlorophenyl)acetamido]-3-methyl-3-cephem-4-carboxylate
p-Nitrobenzyl 7-[$\alpha$-amino-(4-hydroxyphenyl)acetamido]-3-methyl-3-cephem-4-carboxylate
p-Nitrobenzyl 7-($\alpha$-aminophenylacetamido)-3-methyl-3-cephem-4-carboxylate
p-Nitrobenzyl 7-[(1-tetrazole)acetamido]-3-methyl-3-cephem-4-carboxylate
p-Nitrobenzyl 7-[(2-thiophene) acetamido]-3-methyl-3-cephem-4-carboxylate
p-Nitrobenzyl 7-[(3-thiophene)acetamido]-3-methyl-3-cephem-4-carboxylate
p-Nitrobenzyl 7-($\alpha$-aminophenylacetamido)-3-methyl-3-cephem-4-carobxylate hydrochloride
p-Nitrobenzyl 7-($\alpha$-aminophenylacetamido)-3-methyl-3-cephem-4-carboxylate tosylate
p-Nitrobenzyl 7-($\alpha$-aminophenylacetamido)-3-methyl-3-cephem-4-carboxylate nitrate
p-Nitrobenzyl 7-amino-3-methyl-3-cephem-4-carboxylate sulfate This invention is further illustrated by the following specific examples. The following materials are used in the process of this invention. 26 The trypticase Soy Broth is a general purpose medium having the following compositions in grams per liter of distilled water:

| | |
|---|---|
| Trypticase Peptone | 17.0 |
| Phytone Peptone | 3.0 |
| Sodium Chloride | 5.0 |
| Dipotassium Phosphate | 2.5 |
| Dextrose | 2.5 |
| Final pH 7.3± | |

The Trypticase Soy Broth was obtained from Baltimore Biological Laboratories, Cockeyville, Md., 21030. The medium was prepared as described in the BBL Manual of Products and Laboratory Procedures, 5th Ed. 1973, page 151.

The Amberlite XAD resins employed herein are nonpolar polystyrene polymer resins obtained from Rohm and Haas. The XAD-4 resin has a surface area of 750 square meters per gram. The XAD-2 resin has a surface area of 330 square meters per gram.

EXAMPLE 1

Preparation of the Cephalosporin Esterase from
*Bacillus subtilis*

A lyophile pellet of *Bacillus subtilis* culture NRRL B8079 was used to inoculate 50 ml. of 3 percent sterile Trypticase Soy Broth (Difco) medium in a 250 ml. Erlenmeyer flask. After shaking for 8 hours at 37°C. and 250 rpm on a rotary shaker, the vegetative broth culture was used to provide a 5 percent (volume/volume) vegetative inoculum for more flasks of sterile broth. After incubating the second series of vegetative flasks for 18 hours under the above described conditions, the broth culture was used to provide a 0.6 percent inoculum for 500 ml. Erlenmeyer flasks containing 150 ml. of Trypticase Soy Broth (Difco) medium. After incubating for 24 hours at 30°C., the flasks were pooled and the resulting 40 L. of broth culture were centrifuged and 308.7 gm (wet weight) of cells were collected. The cells were suspended in 1 L. of 0.05 M phosphate buffer, pH 6.8, and centrifuged at 5,000 rpm. The collected cells were suspended in 475 ml. of the same buffer and sonicated for 15 minutes. The sonicated cell suspension was centrifuged for 25 minutes at 15,000 rpm. To the resulting supernatant was added ammonium sulfate to 0.8 percent saturation, thus causing the protein to precipitate. The resulting precipitate was collected by centrifugation, was resuspended in 300 ml. of 0.05 M phosphate buffer and the suspension was dialyzed against the same buffer. The resulting dialyzate was lyophilized to give 0.6 g. of powdery esterase preparation. Lowery protein analysis of the preparation gave 0.46 mg. of protein per mg. of preparation.

EXAMPLE 2

Preparation of Cephalexin from Cephalexin tosylate PNB ester With the *B. subtilis* Esterase Preparation To 1 L. of 0.05 M phosphate buffer, pH 6.8, was added 2.5 percent of a *B. subtilis*, NRRL B8079, esterase preparation produced as in Example 1 and 500 mg. of cephalexin tosylate PNB ester. After shaking for 18 hours at 30°C., the pH of the reaction mixture was adjusted with 0.1 N HCl to 2.5 and the mixture was passed over a 2.5 × 70 cm. column of XAD-4 resin. The cephalexin produced in the above reaction was adsorbed on the column. The column was washed with 2 L. of deionized water and the cephalexin was then eluted with methanol. Concentration of the antibiotic containing methanolic eluate fractions gave 326 mg. of cephalexin, N-tosylate. The nmr, uv, infrared spectra, and antimicrobial activity of the material were identical to those of authentic material. Paper chromatographic bioautography of the sample [solvent system, n-butanol:acetic acid:water (3:1:1); assay organism, *Sarcina lutea*]*gave one zone of inhibition whose $R_f$ value was identical to that of authentic cephalexin.

EXAMPLE 3

Preparation of 7-ADCA from 7-ADCA para-Nitrobenzyl Ester Hydrochloride with the *B. subtilis* Esterase Preparation To 1 L. of 0.05 M. phosphate buffer, pH 6.8, was added 2.5 g. of a *B. subtilis*, NRRL B8079, esterase preparation and 500 mg. of 7-ADCA para-nitrobenzyl ester hydrochloride. After shaking for 18 hours at 37°C., the pH of the reaction mixture was adjusted with 0.1 N HCl to 2.5 and passed over a 3.5 × 60 cm. column of XAD-2 resin. The 7-ADCA produced in the above reaction was adsorbed on the column. Elution of the column with water gave 800 mg. of a mixture of 7-ADCA and inorganic salts. This material was dissolved in 200 ml. of water, the pH of the solution adjusted to 6.5 with 0.2 N sodium hydroxide, and the solution passed over a 2.0 × 60 cm. column of XAD-2 resin. The impure 7-ADCA was adsorbed on the column. Elution of the column with 1 L. of water gave 7-ADCA, 76.6 mg. free to salts. The nmr of this material was identical to that of authentic 7-ADCA. A paper chromatographic bioautography of the sample after treatment with phenoxyacetyl chloride vapors, [solvent system, n-butanol:acetic acid:water, (3:1:1); assay organism, *Bacillus subtilis*]*gave one zone of inhibition whose $R_f$ value was identical to that of deacetoxycephalosporin V.

I claim:
1. A process for removing the p-nitrobenzyl group from a cephalosporin ester of the formula

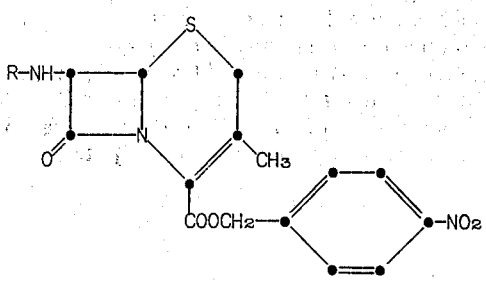

to provide a cephalosporin acid of the formula

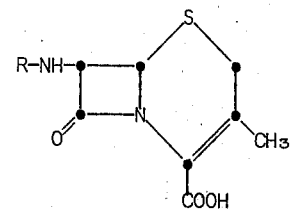

wherein R is hydrogen, 1,4-cyclohexadienylacetyl, mandeloyl, 4-aminophenylacetyl, 4-chlorophenylacetyl, 4-hydroxyphenylacetyl, phenylacetyl, 4-aminophenoxyacetyl, 4-chlorophenoxyacetyl, 4-hydroxyphenoacyacetyl, phenoxyacetyl, 4-aminophenylglycyl, 4-chlorophenylglycyl, 4-hydroxyphenylglycyl, phenylglycyl, 1-tetrazoleacetyl, 2-thiopheneacetyl, 3-thiopheneacetyl, or the hydrobromide, hydrochloride, nitrate sulfate or tosylate salt thereof when R is hydrogen, phenylglycyl, 4-aminophenylglycyl, 4-chlorophenylglycyl, or 4-hydroxyphenylglycyl; which comprises reacting said ester in an aqueous medium at 25° to 40°C. with an esterase enzyme produced by a microorganism selected from the group consisting of *Bacillus cereus, Bacillus circulons, Bacillus licheniformis* ATCC 7072 or *Bacillus subtilis*, and recovering said cephalosporin acid.

2. The process of claim 1 wherein the p-nitrobenzyl ester is incubated in the presence of the microorganism *Bacillus cereus, Bacillus circulons, Bacillus licheniformis* ATCC 7072 or *Bacillus subtilus*.

3. The process of claim 2 wherein the organism is *Bacillus subtilus*.

4. The process of claim 3 wherein the organism is *Bacillus subtilis* NRRL B8079.

5. The process of claim 4 wherein R is hydrogen and the ester is a hydrochloride or tosylate salt.

6. The process of claim 4 wherein R is phenylglycyl and the ester is a tosylate salt.

7. The process of claim 4 wherein R is phenylacetyl.

8. The process of claim 4 wherein R is phenoxyacetyl.

9. The process of claim 4 wherein R is 2-thiopheneacetyl.

10. The process of claim 4 wherein R is mandeloyl.

11. The process of claim 4 wherein R is 1,4-cyclohexadienyl.

12. The process of claim 4 wherein R is 1-tetrazolylacetyl.

13. The process of claim 1 wherein the p-nitrobenzyl ester is reacted with an esterase enzyme isolated from the microorganism *Bacillus cereus*, *Bacillus circulons*, *Bacillus licheniformis* ATCC 7072 or *Bacillus subtilis*.

14. The process of claim 13 wherein the p-nitrobenzyl ester is reacted with the esterase enzyme isolated from the microorganism *Bacillus subtilis*.

15. The process of claim 14 wherein the esterase enzyme is isolated from *Bacillus subtilis* NRRL B8079.

16. The process of claim 15 wherein R is hydrogen and the ester is a hydrochloride or tosylate salt.

17. The process of claim 15 wherein R is phenylglycyl and the ester is a tosylate salt.

18. The process of claim 15 wherein R is phenylacetyl.

19. The process of claim 15 wherein R is phenoxyacetyl

20. The process of claim 15 wherein R is 2-thiopheneacetyl.

21. The process of claim 15 wherein R is mandeloyl.

22. The process of claim 15 wherein R is 1,4-cyclohexadienyl.

23. The process of claim 15 wherein R is 1-tetrazolylacetyl.

* * * * *